United States Patent [19]

Pearsall et al.

[11] Patent Number: 5,723,140
[45] Date of Patent: Mar. 3, 1998

[54] METHOD FOR TREATING PRESSURE ULCERS

[76] Inventors: Charles W. Pearsall, 7 W. Highpoint Rd., Stuart, Fla. 34996; Manuel Caldera, 74-900 Hwy. 111, Suite 221, Indian Wells, Calif. 92210

[21] Appl. No.: 594,087

[22] Filed: Jan. 30, 1996

[51] Int. Cl.$^6$ .................................................. A61K 33/40
[52] U.S. Cl. ........................ 424/404; 424/402; 424/613; 424/615
[58] Field of Search .............................. 424/402, 404, 424/613, 615

[56] References Cited

U.S. PATENT DOCUMENTS

| | | | |
|---|---|---|---|
| 5,097,556 | 3/1992 | Engel et al. ................................ | 8/158 |
| 5,181,399 | 1/1993 | Engel et al. ................................ | 68/13 |
| 5,241,720 | 9/1993 | Engel et al. ................................ | 8/158 |
| 5,493,743 | 2/1996 | Schneider et al. ......................... | 8/149.1 |
| 5,567,444 | 10/1996 | Hei et al. ................................... | 424/613 |

OTHER PUBLICATIONS

Gasanor, Derwent, #95/065199 (1995).
Heggers, Biosis, #92: 24835 (1992).
Derwent #91/211581 (1991).

*Primary Examiner*—James H. Reamer
*Attorney, Agent, or Firm*—Aquilino & Welsh

[57] ABSTRACT

A method for treating an individual to prevent the occurrence of pressure ulcers and facilitate the healing of previously existing pressure ulcers. In accordance with the present invention, a responsible individual must first determine which linens will contact pressure points on the individual as the individual lies upon a support surface. Once the appropriate linens are determined, they are prepared by cleaning the linens in ozonated wash water to limit chemical residuals and maintain neutral pH levels on the linens, wherein the linens exhibiting no chemical residuals and neutral pH cause no chemical reaction with the skin of the individual. Finally, the linens are placed into use so that they contact the skin of the individual at pressure points.

15 Claims, No Drawings

METHOD FOR TREATING PRESSURE ULCERS

BACKGROUND OF THE INVENTION

1. Field of the Invention

The invention relates to a method for treating individuals to reduce the occurrence of pressure ulcers in and to improve the healing process for those individuals already suffering from pressure ulcers. More particularly, the invention relates to a method for treating individuals by exposing the skin of the individuals to health care linens that have been cleaned in ozonated water.

2. Background of the Invention

Pressure ulcers, that is, bedsores, often occur in bedridden and immobile patients as a result of long periods of time spent in one position. The ulcers are caused by the pressure from the body weight of the patient. The pressure causes skin surfaces and deeper tissue layers to restrict blood flow to the points of contact. The application of this pressure over an extended period of time causes ulcers commonly referred to as pressure ulcers.

Pressure ulcers are painful and normally heal very slowly. They can be prevented in some cases by proper nutrition and patient care, as well as prompt attention to symptoms when they appear. Treating pressure ulcers once they appear is time consuming and expensive. Currently, patients are treated by physically moving or turning the patients several times a day. Each time the patient is turned the affected areas are cleaned and the dressings applied to the affected areas are changed. Frequently, pressure ulcers are also treated with hydrotherapy (i.e., whirlpools). Using these techniques it can take weeks to many months before the pressure ulcers are properly healed.

Estimates suggest that the treatment of pressure ulcers costs between $1.5 and 3.5 billion annually in the United States. With this figure in mind, it is a general feeling among practitioners that the incidence of pressure ulcers is widely under reported by facilities, since it is an indication that less than adequate care is being provided to their patients. In some cases, where a sudden surge in pressure ulcers is noted, facilities have been known to investigate possible changes or reductions in processed linen quality from the laundry. However, these investigations have all been directed to conventional laundering processes.

Traditional washing methodology in health care and long term care facilities requires the use of a series of caustic chemicals and high temperature wash water for processing health care linens. The chemicals include chlorine bleach (sodium hypochlorite), alkali, surfactants, sours, and softeners. In addition, the wash water temperatures generally reach temperatures as high as 140° F. to 180° F.

The necessary use of harsh chemicals and very high wash water temperatures makes it difficult to effectively clean health care linens. For example, improper washing techniques, resulting from poor training, very often produce health care linens retaining the harsh chemicals used to clean the linens. Similarly, the limitations of conventional commercial washers results in health care linens containing residuals of the chemicals used to clean the linens. These avoidable and unavoidable events result in linens containing residual chemicals and combine to create the potential for skin irritation due to textile contact. Such contact is believed to be a causative factor in the development of pressure ulcers in individuals confined to their beds for extended periods of time. Further, when individuals exhibiting skin irritation or pressure ulcers are exposed to health care linens containing these residual chemicals, the residual chemicals can delay the healing process through continued irritation.

The chemical residuals and hard wash water quality also cause the linens to assume a rougher feel. Although softeners are often added in the final stages of the wash process, they do not remove the chemical residuals, and the textiles can still exhibit stiff, irritating qualities which cause pressure ulcers and retard the healing process for those individuals already suffering from pressure ulcers.

In view of the shortcomings of the prior attempts to prevent the development of pressure ulcers and to treat those individuals already exhibiting pressure ulcers, a need continues to exists for a treatment method whereby the formation of pressure ulcers is minimized and the healing rate of existing pressure ulcers is improved. The present invention provides such a method.

SUMMARY OF THE INVENTION

It is, therefore, an object of the present invention to provide a method for treating an individual confined to a bed for an extended period of time to prevent the occurrence of bedsores. In accordance with the present invention, a responsible individual must first determine which linens will contact pressure points on the individual as the individual lies upon a support surface. Once the appropriate linens are determined, they are prepared by cleaning the linens to limit chemical residuals and maintain neutral pH levels on the linens, wherein the linens exhibiting no chemical residuals and neutral pH cause no chemical reaction with the skin of the individual. Finally, the linens are placed into use so that they contact the skin of the individual at pressure points.

It is another object of the present invention to provide a method for treating pressure ulcers wherein the linens are cleaned in ozonated water.

It is a further object of the present invention to provide a method for treating pressure ulcers wherein the linens are hospital gowns.

It is also an object of the present invention to provide a method for treating pressure ulcers wherein the linens are bed pads.

It is another object of the present invention to provide a method for treating pressure ulcers wherein the linens are bed sheets.

It is also a further object of the present invention to provide a method for treating pressure ulcers wherein the linens are diapers.

It is a further object of the present invention to provide a method for treating pressure ulcers wherein surfactants are added to the wash water.

It is also an object of the present invention to provide a method for treating pressure ulcers wherein sodium hypochlorite, $H_2O_2$ or oxygen bleach is added to the wash water.

It is another object of the present invention to provide a method for treating pressure ulcers wherein the wash water is at a temperature below about 105° F.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

The present method is provided for the treatment of individuals confined to a bed for an extended period. The method is also provided for the treatment of other individuals who are susceptible to pressure ulcers (for example, wheelchair users) or may already be suffering from pressure ulcers. Specifically, the invention provides a method whereby health care linens used for bedridden individuals are cleaned with ozonated wash water to reduce the occurrence of pressure ulcers and to treat those individuals suffering from previously existing pressure ulcers. The terms "health care linens" and "linens" are used throughout this application and should be understood to refer to regularly cleaned and reused textiles employed by hospitals and other health care facilities (for example, nursing homes) as bed sheets, hospital gowns, bed pads, diapers, etc.

In accordance with the present invention, the treatment is initiated by first determining which health care linens will contact pressure points on the individual as the individual lies, or sits, upon a support surface. The most common pressure points are the shoulder blades, hips, heels, and buttocks, although other portions of a patient's body may be affected by pressure ulcers depending upon the patient's condition. Generally, the bed sheets, hospital gowns and bed pads will contact the pressure points of individuals confined to a bed for an extended period of time. Similarly, the individual's clothing will generally contact pressure points in individuals confined to wheelchairs.

Once the appropriate linens are identified, the linens are prepared by cleaning the linens in ozonated wash water. Cleaning the linens in ozonated wash water prevents, or substantially limits, the retention of chemical residuals and maintains the linens at a neutral pH (approximately 7). The lack of chemical residuals in health care linens cleaned with ozonated wash water precludes the occurrence of detrimental chemical reactions between the linens and the individual's skin. In addition, the neutral pH of the linens cleaned with ozonated wash water substantially matches the pH of human skin and, once again, the linens produce no chemical reactions with the skin of the individual based upon a difference in pH.

The preferred process for cleaning textiles with ozonated water is set forth in U.S. Patent application Ser. No. 08/279, 019, entitled "Ozone Assisted Laundry Wash Process And Waste Water Treatment System" (Issue Fee paid on Nov. 7, 1995), which is incorporated herein by reference. The application was filed Jul. 22, 1994 by Keith R. Schneider et al. and is assigned to TRI-O-CLEAN LAUNDRY, INC. the assignee of this application. Other processes for cleaning textiles with ozonated water are set forth in U.S. Pat. No. 5,097,556, to Engel et al., entitled "Laundry Waste Water Treatment And Wash Process", U.S. Pat. No. 5,181,399, to Engel et al., entitled "Laundry Waste Water Treatment And Wash Apparatus", U.S. Pat. No. 5,241,720, to Engel et al., entitled "Laundry Waste Water Treatment And Wash Process", which are also incorporated herein by reference.

In contrast, we have discovered that health care linens cleaned in conventional manners may exhibit a high pH, and the distinct difference in the pH of the exposed skin and the applied linens causes irritation of the skin. Specifically, alkali and bleach, chemicals commonly used in cleaning health care linens, have elevated pH levels, while human skin has a neutral pH of approximately 7 (seven). The difference in pH is broadened as people get older, since the pH of older individuals tends to go down to approximately 6 (six). When the elevated pH of health care linens comes into contact with the skin of an individual, the residual chemicals are activated. Specifically, moisture from urine, feces, or perspiration activates the residual chemicals in the health care linens and causes skin irritation. The skin irritation may become exacerbated over time due to continued contact and movement against linens, thereby resulting in undesirable pressure ulcers.

As stated previously, conventional cleaning techniques require high temperature wash water. In accordance with the present invention, the wash water temperature need not be heated to the extent necessary in conventional cleaning techniques. Specifically, when cleaning with ozonated water it is necessary to achieve a dissolved ozone residual in the wash water feeding the washing machine. To this end, wash water temperatures of more than 105° F. are not desirable, since they make the ozone react very quickly and reduce the effectiveness of the ozone. The ozonated wash water temperature should, therefore, be maintained between approximately 70° F. and approximately 100° F.

Sodium hypochlorite is preferably added to the ozonated wash water during the cleaning process. The sodium hypochlorite assists in the whitening, stain removal, and disinfection of the linens, and is destroyed by the ozone before the extraction process. The extraction process is the last stage of the rinse cycle where the washing machine spins rapidly to extract the remaining wash water from the linen via centrifugal action. The sodium hypochlorite can be substituted with hydrogen peroxide or oxygen bleach, when the hydrogen peroxide or oxygen bleach are used in proper amounts, without departing from the spirit of the present invention. It should be understood that, while the sodium hypochlorite has an elevated pH level, the residual dissolved ozone in the wash water oxidizes the sodium hypochlorite levels during the rinsing events. Consequently, little or no chlorine retention is exhibited by the linens.

In addition to disinfecting the health care linens, the ozonated wash water assists in loosening oxidizable soil and stains (protein based) that are very common in health care linens. Specifically, the mechanical action of the washing machine dislodges soil and stains within the linens. The dislodged soil and stains then become suspended in the wash water. As such, a small amount of surfactant may be added to the wash water to maintain the soil and stains in suspension, and avoid soil redeposition or greying of the linens.

Once the health care linens are appropriately cleaned with ozonated wash water, the linens are used in a manner so that they contact the skin of the individual at pressure points. These linens may be used by individuals who do not exhibit any pressure ulcers but will be bedridden, or similarly confined, for an extended period of time. In addition, the linens may be used by individuals suffering from pressure ulcers in an attempt to treat the lesions.

While the instant treatment method presents a novel departure from prior methods for treating health care linens, it should be understood that accepted linen management standards are followed when preparing linens in accordance with the present invention. For example, heavily soiled items are washed in slightly longer formula times and require more bleach and surfactants. For this reason, diapers and bedpans are washed separately from sheets and towels.

In addition, the washing machines are properly loaded so as not to overload the machines. As such, machines are only loaded to between approximately 80% and 90% of their rated capacities and weighing of linens is, therefore, recommended prior to washing machine loading. Further, linens are shaken out before they are loaded in the machine to facilitate complete cleaning.

The resulting health care linens cleaned according to accepted linen management standards, coupled with the use of ozonated wash water, are deodorized, hypo-allergenic, and soft. The resulting linens contain little or no chemical residuals and exhibit neutral pH. Therefore, the resulting linens, having a neutral pH level and little or no chemical residuals, do not chemically react with an individual's sensitive skin, even after long periods of contact in moist environments. The lack of chemical reaction with the skin of an individual prevents the occurrence of pressure ulcers and facilitates the healing of previously existing pressure ulcers. In addition, the softer nature of the resulting linens reduces irritations from rubbing and provides greater individual comfort. This further reduces the occurrence of pressure ulcers and speeds the healing process for those individuals suffering from pressure ulcers.

While the preferred embodiment has been shown and described, it will be understood that there is no intent to limit the invention by such disclosure, but rather, is intended to cover all modifications and alternate constructions falling within the spirit and scope of the invention as defined in the appended claims.

We claim:

1. A method for treating an individual to prevent the occurrence of pressure ulcers and facilitate the healing of previously existing pressure ulcers, comprising the following steps:

determining which linens will contact pressure points on the individual as the individual rests upon a support surface;

preparing the linens by cleaning the linens in ozonated wash water to limit chemical residuals and maintain neutral pH levels on the linens, wherein the linens cleaned in ozonated wash water exhibit no chemical residuals and neutral pH, and cause no chemical reaction with the skin of the individual; and placing the linens into use so that they contact the skin of the individual at pressure points.

2. The method according to claim 1, wherein the linens are hospital gowns.

3. The method according to claim 1, wherein the linens are bed pads.

4. The method according to claim 1, wherein the linens are bed sheets.

5. The method according to claim 1, wherein the linens are diapers.

6. The method according to claim 1, further including the step of adding surfactants to the wash water.

7. The method according to claim 1, further including the step of adding sodium hypochlorite to the wash water.

8. The method according to claim 1, wherein the wash water is at a temperature below about 105° F.

9. The method according to claim 1, wherein the linens are hospital gowns.

10. The method according to claim 1, wherein the linens are bed pads.

11. The method according to claim 1, wherein the linens are bed sheets.

12. The method according to claim 1, wherein the linens are diapers.

13. The method according to claim 1, further including the step of adding surfactants to the wash water.

14. The method according to claim 1, further including the step of adding sodium hypochlorite to the wash water.

15. The method according to claim 1, wherein the wash water is at a temperature below about 105° F.

* * * * *